United States Patent [19]

Allen et al.

[11] Patent Number: 4,962,172

[45] Date of Patent: Oct. 9, 1990

[54] ABSORBENT PRODUCTS AND THEIR MANUFACTURE

[75] Inventors: Adrian S. Allen, North Yorkshire; David Farrar; Peter Flesher, both of West Yorkshire, all of England

[73] Assignee: Allied Colloids Ltd., Great Britain

[21] Appl. No.: 123,572

[22] Filed: Nov. 20, 1987

[30] Foreign Application Priority Data

| Nov. 20, 1986 | [GB] | United Kingdom | 8627729 |
| Apr. 10, 1987 | [GB] | United Kingdom | 8708601 |
| Apr. 10, 1987 | [GB] | United Kingdom | 8708690 |
| Apr. 10, 1987 | [GB] | United Kingdom | 8708599 |
| Aug. 4, 1987 | [GB] | United Kingdom | 8718396 |

[51] Int. Cl.$^5$ ............................ C08F 220/10
[52] U.S. Cl. ............ 526/318.42; 526/320; 526/342; 526/347
[58] Field of Search ............ 526/273, 318.5, 318.42, 526/320, 342, 347

[56] References Cited

U.S. PATENT DOCUMENTS

| Re. 30,029 | 6/1979 | Smith . |
| 3,311,583 | 3/1967 | Bearden . |
| 3,884,964 | 5/1975 | Otrhalek et al. . |
| 3,926,891 | 12/1975 | Gross et al. . |
| 3,980,663 | 9/1976 | Gross . |
| 3,995,998 | 12/1976 | Rowland et al. ............ 524/733 |
| 4,041,121 | 8/1977 | Smith . |
| 4,057,521 | 11/1977 | Gross . |
| 4,066,584 | 1/1978 | Allen et al. . |
| 4,104,214 | 8/1978 | Meierhoefer . |
| 4,218,692 | 8/1980 | Cremoux . |
| 4,351,922 | 9/1982 | Yoshida et al. ............ 526/318.3 |
| 4,431,769 | 2/1984 | Yoshida et al. ............ 524/555 |
| 4,524,186 | 6/1985 | Nagase ............ 526/329.7 |

FOREIGN PATENT DOCUMENTS

| 0213799 | 11/1987 | European Pat. Off. . |
| 0264208 | 4/1988 | European Pat. Off. . |
| 0272074 | 6/1988 | European Pat. Off. . |
| 7719027 | 1/1978 | France . |
| 473734 | 2/1972 | Japan ............ 526/273 |
| 56-161413 | 12/1981 | Japan . |
| 0084819 | 5/1983 | Japan ............ 526/273 |
| 63-28912 | 2/1988 | Japan . |
| 783755 | 9/1957 | United Kingdom ............ 526/273 |
| 0940766 | 11/1963 | United Kingdom . |

OTHER PUBLICATIONS

Chemical Abstracts, vol. 96, No. 20, May 1982, p. 35, Abstract No. 163649q, Columbus, Ohio, US; and JP-A-81 161 413 (KAO Soap Co., Ltd.) 11-12-1981.
Patent Abstracts of Japan, vol. 6, No. 19 (C-90) [897], 3rd Feb. 1982; and JP-A-56 141 308 (Nippon Hatsujiyou K.K. 5-11-1981.

Primary Examiner—Joseph L. Schofer
Assistant Examiner—N. Sarofin
Attorney, Agent, or Firm—Ostrolenk, Faber, Gerb & Soffen

[57] ABSTRACT

A water absorbent water insoluble polymeric element, such as fibre, film, coating, bonding layer or foam, is made by forming a substantially linear polymer by polymerization of water soluble ethylenically unsaturated monomer blends comprising carboxylic and hydroxylic monomers and then reacting the carboxylic and hydroxylic monomers in the linear polymer to form internal cross links within the polymer.

22 Claims, No Drawings

ABSORBENT PRODUCTS AND THEIR MANUFACTURE

This invention relates to water absorbent, water insoluble, polymeric elements that are useful for absorbing aqueous fluids, for instance urine.

It is well known to provide water absorbent, water insoluble, polymeric material in the form of particles by polymerising water soluble monomer or monomer blend, for instance acrylic acid, in the presence of a polyethylenically unsaturated monomer, that will be copolymerised into the polymeric backbone so as to cause cross linking and render the polymer insoluble in water. Ionic cross linking, for instance by aluminium ions, between pendant groups is also known. Since the cross linking occurs substantially simultaneously with the polymerisation, the normal methods do not permit the polymer to be shaped by extrusion or coating techniques after polymerisation. Instead it is made in its desired final shape, e.g., as beads by reverse phase polymerisation, or in bulk form and is then comminuted to particles. There are, however, many instances where it would be desirable to be able to provide the polymer in the form of a film, fibre or other shaped element.

In U.S. Pat. No. 3,926,891, 3,980,663 and 4,057,521 various processes are described in which a substantially linear acrylic polymer is shaped and is then cross linked through its pendant groups. In U.S. Pat. No. 3,926,891 and 3,980,663 a shapable solution of substantially linear acrylic polymer is formed, a cross linking agent is mixed into the solution, the solution is shaped and then the cross linking reaction is performed. In practice the method is not very successful. It seems to be difficult or impossible in practice to achieve uniform distribution of the cross linking agent in the polymer solution (which is usually relatively viscous) and, in any event, during the shaping and cross linking operations the cross linking agent is liable to migrate through the solution, and the degree of cross linking is difficult to control accurately. Accordingly it has apparently been difficult or impossible to obtain products having a controllable and uniform degree of water absorption by this technique.

In U.S. Pat. No. 4,057,521 it is proposed that the linear polymer should be a copolymer of, for instance, acrylic acid and N-methylol acrylamide, with the intention that cross linking should be caused, after shaping of the solution, by condensation of a carboxylic acid group with the methylol acrylamide group. It is proposed that the condensation would result in the elimination of a molecule of water, and thus the formation of an ester linkage containing a nitrogen atom in the linkage. In practice however other reactions will certainly occur in parallel with it, and possibly in preference to it. In particular there will inevitably be significant formation of bis-acrylamide groups, with liberation of formaldehyde. The presence of such groups, and the liberation of formaldehyde, renders the process unacceptable for many of the uses of water absorbent polymeric materials, for instance in diapers.

Another apparently unsuccessful proposal is made in FR 2,355,929. In this, a diol or diamine is mixed into an aqueous solution of polyacrylic acid which is then shaped and the shaped article is heated to cause condensation between the difunctional cross linking agent and the polyacrylic acid. Again, this suffers from the same disadvantages of difficulty of achieving a uniform distribution of the cross linking groups through the polymer. Comonomers that have been mentioned in these patents include certain hydroxyalkyl acrylate monomers, but they appear to be unreactive during the described processes.

In addition to these proposals that have, apparently, not been commercialised, various shaped absorbent particles have been made, especially in the form of films or fibres.

One type of absorbent fibre is formed by hydrolysing the outer surfaces of polyacrylonitrile fibres so as to form a sheath of linear water soluble polymer and a core of insoluble polymer that gives the fibre strength. Another process comprises precipitating a water soluble polymer onto an insoluble substrate such as cotton (see e.g. U.S. Pat. No. 4,218,692 and 4218692). Another process involves injecting an aqueous solution of water soluble polymer into a stream of viscose just prior to extruding the viscose as a fibre or filament (see e.g. U.S. Pat. No. 4,066,584, 4,104,214 and Re 30,029). All these methods suffer from the disadvantage that the fibres incorporate a substantial amount of a material (polyacrylonitrile, viscose or cotton) that is of low absorbency and so the capacity of the fibres, on a weight basis, is relatively low compared to existing absorbent polymers. Also the soluble surface of many of the fibres tends to cause stickiness during use.

In practice therefore it has proved difficult or impossible to make or handle films or fibres of appropriate water absorbent polymeric material on large scale manufacturing equipment, and the absorbency and other performance properties of the films and fibres tends to be inferior compared to conventional particulate absorbent polymers.

There remains an urgent need for fibres, films or other shaped articles of water insoluble water swellable polymer that can be made reliably by large scale, high speed, manufacturing processes and that have satisfactory absorbency properties compared to the absorbency properties of conventional particulate water swellable polymers.

A water absorbent, water insoluble, polymeric element according to the invention is an element that has been made by forming a substantially linear polymer by polymerisation of a water soluble ethylenically unsaturated monomer blend comprising monomer that provides carboxylic acid monomer groups and monomer that provides hydroxylic groups that can react with the carboxylic acid groups to form ester linkages that contain only carbon and oxygen atoms in the linkages, and then reacting the said carboxylic and hydroxylic groups to form the said cross linkages.

The invention therefore eliminates the need to incorporate an external cross linking agent into a solution of pre-formed linear polymer, and instead cross linking is obtained by reaction between pendant groups on the pre-formed polymer. The instability and other undesirable consequences of relying upon groups such as methylol acrylamide is avoided by utilising monomers that do not incur the risk of, for instance, formaldehyde liberation and that, instead, react to form ester cross linkages that are free of nitrogen atoms in the linkage and that, instead, contain only carbon and oxygen atoms in the linkages. Such linkages appear to be entirely satisfactory from the toxicological point of view.

However the main advantage of the invention is that it is possible, for the first time, conveniently to make the substantially linear polymer in any convenient manner (for instance as a bulk solution) and then to shape the substantially linear polymer into a desired final shape, and then to effect the cross linking in a very controlled manner to give a product that is toxicologically entirely acceptable. Generally therefore the substantially linear polymer is made in solution, generally aqueous solution, and this solution is shaped before the formation of the cross linkages The monomers used for providing the cross links must therefore be such that it is possible to form the polymer and to shape the polymer without cross linking occurring, and to cause substantially complete cross linking by appropriate treatment of the shaped polymer.

Suitable carboxylic monomers are (meth) acrylic acid or any of the other conventional ethylenically unsaturated carboxylic acids, optionally with 2-acrylamido-2-methyl propane sulphonic acid or any of the other conventional ethylenically unsaturated sulphonic acids, or allyl sulphonate. Carboxylic and sulphonic monomers may be present in the final polymer in free acid or water soluble salt form, suitable salts being formed with ammonia, amine or alkali metal. The proportion of salt and free acid groups can be adjusted after formation of the cross linked polymer or after polymerisation of the linear polymer or before polymerisation. Generally the ratio of free carboxylic acid/alkali metal or other salt carboxylic acid groups in the final polymer (and often also in the monomers that are used to form the linear polymer) from 1:1 to 1:10. The ratio is usually at least 1:2 and often 1:3. It is generally below 1:6 and often below 1:5.

In many instances it is desirable, in order to promote the internal cross linking reaction, that some at least of the carboxylic acid groups should be present as free. acid groups before the cross linking occurs. For instance, for this purpose, it may be adequate for 10 to 75%, preferably 25 to 75%, of the acid groups to be in free acid form before the cross linking occurs.

Although the linear polymer is generally made by polymerisation of carboxylic acid monomer (in free acid or salt form) it is also possible to make the polymer by polymerisation of monomer that can be subsequently reacted to form the carboxylic acid monomer. For instance the carboxylic acid (as free acid or salt form) groups that are to be present in the cross linked monomer may be present initially in the linear polymer in the form of hydrolysable ester groups, such as methyl ester groups, that can then be hydrolysed while in the form of a linear polymer to yield carboxylic acid (free acid or salt) groups.

The monomer that provides hydroxylic groups for internal esterification with the carboxylic acid groups is selected from ethylenically unsaturated monomers that can react with carboxylic acid groups to form the desired ester linkages. The monomer must be one that does not form the ester cross links during the initial polymerisation to make the linear polymer, and that does not form any substantial number of cross links during the shaping of the linear polymer.

The hydroxyl groups may be generated in the linear polymer by, for instance, breaking a ring such as a glycidyl or epoxide substituted vinyl monomer, but preferred monomers contain free hydroxyl groups and are selected from vinyl alcohol, allyl alcohol and hydroxy alkyl esters of vinyl carboxylic monomers The preferred esters are hydroxy alkyl esters of (meth) acrylic acid. The monomer may be monofunctional, containing a single hydroxyl group, or may be polyfunctional, containing two, three or more hydroxyl groups per vinyl group The hydroxyl alkyl group generally contains from 1 to 10, preferably 1 to 8, carbon atoms. Suitable monomers include hydroxy ethyl (meth) acrylate, hydroxyl propyl (meth) acrylate, di- or tri- alkylene glycol mono (meth) acrylate where the alkylene group is ethylene or propylene, and glyceryl mono (meth) acrylate.

The amount of hydroxy monomer is preferably 0.1 to 15%, generally 1 to 10%, and the amount of carboxylic acid (or salt) is preferably above 50%, and often above 70%. These amounts are by weight based on total monomers. Often the blend is formed of 90-99% acrylic acid (some being in salt form) and 1 to 10% hydroxy alkyl acrylate.

Polymers formed solely from the defined carboxylic acid (as free acid and/or salt) and hydroxyl monomers tend to be rather brittle and it is preferred to include in the polymer plasticising monomers. The use of hydroxy alkyl esters containing 6 to 10 carbon atoms will promote plasticisation but it is generally desirable to include additional plasticising monomer so as to promote plasticisation and improve flexibility of the resultant polymer. The monomers may be aromatic ethylenically unsaturated monomers, such as acrylonitrile or styrenes (e.g., styrene or substituted styrenes), but they are preferably alkyl esters of (meth) acrylic acid or other suitable unsaturated carboxylic acid. Vinyl acetate and other vinyl esters may be used. The alkyl group of the ester generally contains less than 24 carbon atoms and usually 2 or more. Preferred alkyl groups contain 1 to 10 carbon atoms, especially ethyl and also higher alkyl groups such as 2-ethyl hexyl or other C6–C10 alkyl groups. Particularly preferred plasticising monomers are methyl or ethyl (meth) acrylate, butyl (meth) acrylate and 2-ethyl hexyl (meth) acrylate. They are generally present in amounts of at least 2% and often at least 10%. The amount is usually below 50%, and generally below 45%, by weight based on the monomers used for forming the substantially linear polymer.

Other non-ionic monomers that may be used include ethylenically unsaturated monomers that carry a pendant group $-A_mB_nA_pR$ wherein B is ethyleneoxy, n is an integer of at least 2, A is propyleneoxy or butyleneoxy, m and p are each an integer less than n and preferably below 2 and most preferably zero, and R is a hydrophobic group containing at least 8 carbon atoms. The use of 1 to 50% by weight, generally 5 to 30% by weight, of such monomers can give plasticisation and can give improved absorptive capacity and non-tackiness, especially in aqueous electrolytes.

For a full description of suitable values of A, B, R, n, m and p, reference should be made to EP 0213799.

The substantially linear, water soluble, polymer may be formed from the monomer blend in any conventional manner. It may be pre-formed and then dissolved to form a polymer solution. For instance it may be made by reverse phase polymerisation if the monomer blend is soluble in water or by water-in-oil emulsion polymerisation if the blend is insoluble in the water, e.g., at a low pH. However this can incur the risk that the polymer may be contaminated by surfactant and this is undesirable. Preferably therefore the polymer is made by aqueous solution or other solution polymerisation methods. It may have been dried, but preferably not. Generally it is formed by solution polymerisation in the solvent in which it is to be shaped (generally water).

The polymerisation can be conducted in conventional manner in the presence of conventional initiators and/or chain transfer agents to give the desired molecular weight. If the molecular weight of the linear polymer is too low, the physical properties of the article may be inadequate. Generally therefore it is at least 30,000 and preferably at least 100,000 when the article is an extruded film or fibre but lower values, e.g., down to 10,000 or even down to 3,000 may be suitable in some shaping process, e.g., for casting or coating. If the molecular weight if too high it may be difficult to shape an adequately concentrated solution of the polymer as a fibre or film. Generally the molecular weight is below 1 million, usually below 500,000 and preferably below 250,000. However where the shaped article can initially be relatively thick, e.g., a coarse film or fibre that may then be stretched if it is desired to reduce its thickness, higher molecular weights, e.g., up to 10 million or more, are sometimes suitable.

Preferably the substantially linear polymer is, at the time of cross linking, substantially free of unreacted hydroxyl-providing monomer or other cross linking agent. The polymerisation should therefore be conducted in known manner so as to give substantially no free monomer in the polymer solution. The polymer solution generally is a solution in water or in organic solvent (e.g., methanol) or a blend. Preferably the solvent is water The polymer concentration is generally at least 5% and is usually below 50%. Often it is 10 to 40% and typically is 20 or 25% to about 35%.

After formation of the linear polymer, it is shaped and the cross linking reaction is then caused to occur.

The invention is of particular value when the shaping is by extrusion of the solution of the substantially linear polymer to provide a shaped element that has one dimension at least five times a second dimension. For instance films and fibres can be made. This shaping can involve coating the solution on a surface but generally comprises extruding it as a film or fibre. Substantially immediately after extruding or otherwise shaping the solution, the linear polymer is caused to form a uniform solid mixture in the form of an article of the desired shape. The article is initially generally very soft. The conversion of the liquid solution to the soft solid articles can be described as precipitation and may involve solvent evaporation, solvent extraction, or other means of insolubilising the polymer and.

The shaping can be by wet spinning into an organic solvent that removes water, generally acetone, methylethyl ketone or other lower ketone, or into an inorganic aqueous salt solution such as of lithium chloride or aluminium sulphate. Acetone is preferred.

Alternatively it can be by dry spinning. Preferably it remains slightly damp until the final cross linking in order to maintain softness. In a particularly preferred method, an aqueous solution of the linear polymer is dry spun at a temperature above 150° C., often above 200° C, typically 220 to 270° C. to give a product that is substantially dry on the surface but contains at least 10% residual moisture, the dry spun product is stretched and is cured by heating, generally after collecting the stretched fibre or film.

Cross linking can be promoted by incorporating a catalyst in a solution of the polymer or by exposing the shaped polymer to a catalyst (e.g., by passing the polymer through an atmosphere or solution of a catalyst for the esterification reaction). Generally however the esterification is conducted in the absence of added catalyst. The monomers can be selected such that the esterification is effected by irradiation but generally it is effected by heating the shaped substantially linear polymer to a temperature above 150° C. for sufficient time for the cross linking reaction to occur. For instance it may be 170° C. to 200° C. for 5 to 40 minutes. At higher temperatures shorter reaction times are appropriate, for instance 0.1 to 10 minutes at 200 to 250° C. or up to 300° C. Preferred esterification conditions generally involve heating to 200 to 220° C. for, for instance, 1 to 3 minutes.

Additional components may be included in the solution that is to be shaped in order to modify the properties of the final product. For instance, external plasticiser may be incorporated. The amount of materials other than the cross-linked polymer is generally below 20%, preferably below 10%, by weight of the final article.

The shaped element often has a minor dimension (e.g., the thickness of the film or diameter of fibre) below 1 mm, usually below 500 $\mu$m and preferably below 250 $\mu$m. However it is usually unnecessary for it to be smaller than 50 $\mu$m. The element can have a relatively short may or dimension, for instance 1 mm, e.g. in a fibrid, lamella or flake shaped article but generally the final element is a substantially continuous film, a substantially continuous filament, or staple fibre typically having a length of 3 to 100 mm.

The element usually has a gel capacity of at least 50g deionised water, and at least 20g 0.9% NaCl aqueous solution, per gram dry polymer.

The element may be provided with additional surface cross-linking, for instance ionic cross-linking with aluminium or other polyvalent metal compound, in order to improve its rate of absorption of liquids The resultant absorbent elements may be used in any environment where it is desirable to absorb water, and in particular aqueous electrolyte such as urine or other body fluids, for instance as a replacement for part of the cellulosic fibres in diapers, catamenial appliances, incontinence pads or bandages When the articles are in the form of fibres they may be scattered into the cellulosic fibres or a film or, preferably, a woven or nonwoven fabric formed of the filaments or fibres may be incorporated in the diaper or other article.

Wound dressing, absorbent wipes and other fabrics may be formed from fibres part or all of which are in accordance with the invention.

In another method the shaping is by impregnating or coating a solution of the substantially linear polymer on to a film or fibrous core. Thus an absorbent product according to the invention is a fibrous or film product comprising a core and a surface layer of a cross linked, absorbent, polymer formed by cross linking the linear polymer in the manner described above.

The product may be made by sizing the core, as a fibrous or film product, in a solution of the linear polymer, and then cross linking the linear polymer.

The core may be a film but is generally fibrous. It may be a continuous filament or a yarn. It may be formed of, for instance, cotton yarn or it may be a yarn, filament or film of polyester, polypropylene, acrylic, polyamide or other polymeric material.

The dry pick up to the sizing polymer typically is 2-25%, preferably 7-17% by weight.

The linear polymer preferably forms a discontinuous film on the core (so as to improve flexibility) and good results are obtained when the core has a relatively hydrophobic surface and the size is aqueous. Preferably the core is of polyester yarn, filament or film.

Woven or non-woven sheet materials can be sized.

The sized products of the invention can be used in the manufacture of absorbent liners, clothing or fabrics or in the manufacture of articles such as diapers or wound dressings. Sized fibres or yarns can be incorporated into a wide variety of fibre blends in amounts of, e.g., 0.05 to 20% by weight, or articles may be formed solely from the sized fibres. Liners of the invention may be used for food, flower or vegetable packaging, especially in ice packages. It may be used as a horticultural growing medium.

Another absorbent product according to the invention comprises a sheet substrate and an absorbent substrate bonded to it by a cross linked absorbent polymer formed by cross linking the linear polymer in the manner described above.

The product may be made by laminating the absorbent substrate to the sheet substrate while either or both of the facing surfaces of the substrate carry a coating of the linear polymer and then cross linking the linear polymer while bonding the facing surfaces with the polymer.

The linear polymer may initially be dry and may then be wetted and cross linked so as to cause adhesion and cross linking. Generally the linear polymer is applied as a solution and the substrates laminated while one or both of the facing surfaces are wet.

The linear polymer may be applied as an overall coating, e.g., by spread coating or spray, or as a discontinuous coating, e.g., by spray or printing. A pattern of lines or dots, with uncoated areas in between is often particularly useful.

Other absorbent material, e.g., swellable polymer particles or fibres, may be bonded between the substrates by the polymer.

Generally both substrates are absorbent. Generally both are fibrous, often non-woven. Preferably both are paper tissue. If desired one may be formed by depositing fibres on to the other, after application of the polymer. Conveniently the polymer is applied as a laminating solution during the manufacture of laminated paper, in conventional manner.

The product may therefore be used as a laminated kitchen or industrial wipe or as a paper towel or as a wound dressing. It may be used as an absorbent liner, e.g., in diapers or in food, flower or vegetable packaging, especially in ice packages. It may be used as horticultural growing medium.

The amount of linear polymer is generally from 1 to 50% by weight of the laminate (when dry).

Another absorbent product according to the invention comprises a foam having the absorbent polymer substantially uniformly distributed throughout the foam. The foam may consist of the polymer or the polymer may be incorporated in a supporting foam of some other polymeric material, for instance a polyurethane. Thus the shaping may be effected by incorporating a solution of the substantially linear polymer into a foamable composition foaming the composition and cross linking the polymer. Preferably the foamable composition comprises a foamable polymer-forming material preferably a polyurethane prepolymer that preferably is hydrophilic, preferably a polyether polyisocyanate. The amount of the linear polymer typically is 0.03-1, generally 0.05-0.5, parts per part by dry weight of the final dry weight of the foam.

The foam can be used for various absorbent purposes. For instance it may be comminuted and included as part of the absorbent in diapers.

The following are some examples.

EXAMPLE 1

A copolymer comprising 75.7% by weight sodium acrylate, 19.3% by weight of acrylic acid, and 5.0% by weight of hydroxypropyl methacrylate was prepared as a 25% by weight solution in water.

The viscosity of this solution was 113,200 cps (Brookfield RVT at 20 rpm spindle 7 at 20° C.). A 100 micron thick film was prepared of this polymer and heated at 200° C. for 5 minutes after which time the polymer was cross linked and absorbed 250 times its own weight of water.

EXAMPLE 2

A copolymer comprising 69.4% by weight sodium acrylate, 17.6% by weight of acrylic acid, 3.0% by weight of hydroxypropyl methacrylate and 10% by weight of methyl acrylate was prepared as a 20% by weight solution in water. The viscosity of this polymer solution was 26,900 cps (Brookfield RVT at 20 rpm spindle 7 at 20° C.). A 100 micron thick film of this polymer cross linked in 2 minutes at 200° C. and 10 minutes at 180° C. to yield a material that absorbed about 200 times its own weight of water.

EXAMPLES 3 TO 5

Copolymers were prepared as 20% by weight solutions in water comprising 77.7% by weight of sodium acrylate, 18.8% by weight of acrylic acid and 2.5% by weight of the following monomers.

| Example | Comonomer |
|---|---|
| 3 | Hydroxyethyl methacrylate |
| 4 | Tripropyleneglycol mono acrylate |
| 5 | Glyceryl mono acrylate |

Thin (100 micron) films of these copolymers were prepared and heated at 200° C for 5 minutes after which time they were cross linked and showed a high capacity for water and 0.9% sodium chloride solution absorption

EXAMPLE 6

The process of Example 1 can be repeated by extruding a filament of the polymer as an aqueous solution, optionally containing polyethylene glycol 400 as external plasticiser, into acetone and drawing the filament out of the bath, winding with stretching, and heating. Alternatively the polymer solution can be extruded as a filament into warm air, wound while slightly damp and heated.

EXAMPLE 7

A copolymer of composition 69.5/17.5/10/3 parts by weight of sodium acrylate/acrylic acid/methacrylate/hydroxypropyl methacrylate was prepared as a 20% solution in water by polymerisation at 70° C. using azobis cyanovaleric acid as initiator. This polymer solution had a Brookfield viscosity at 25° C. (speed 20 rpm Spindle 6) of 275 poise.

Thin films were prepared from 4% solutions of the polymer and heated at 180° C. and 200° C. for various times then tested for solubility by immersing in water for 5 minutes. It was thus determined that 2 minutes at 200° C. or 10 minutes at 180° C. were required to effect cross linking.

A 10% solution of polymer in water was prepared and used to size two yarn samples - 1:2/20's count cotton and 2:2/167 decitex 34-filament F34 Trevira textured polyester yarn. The yarns were sized on a Roaches Laboratory Sizing machine using the following conditions.

|  | 2/20's count cotton | 2/167 decitex F34 Trevira |
|---|---|---|
| Size Bath temperature (°C.) | 80 | 50 |
| Squeeze pressure (psi) | 12 | 12 |
| Drying cylinder |  |  |
| temperatures (°C.) 1 | 120 | 110 |
| 2 | 115 | 110 |
| 3 | 110 | 105 |
| Speed (meters min$^{-1}$) | 30 | 30 |

The amount of dry polymer on dry yarn was determined from scour loss to be 10.5% by weight on the cotton yarn and 10.3% by weight on the polyester yarn.

0.5 gram swatches of sized and unsized yarns were then placed in an oven preheated and set at 200° C. for 5 minutes then placed in about 200 mls of deionised water for about 1 hour then squeezed to remove surface water. Each swatch was then reweighed. In this way the amount of water absorbed by the size polymer was determined to be

|  | Wt. % water absorbed |
|---|---|
| Sized cotton | 1255 |
| Untreated cotton | 48 |
| Sized Polyester | 1033 |
| Untreated Polyester | 84 |

EXAMPLE 8

A copolymer was formed of 75.7% sodium acrylate, 19.3% acrylic-acid and 5% hydroxyethyl acrylate. An aqueous solution of this can be printed on to a paper tissue. A second tissue can then be applied on to the printed surface while wet and the laminate heated to cause cross linking.

EXAMPLE 9

A copolymer was formed of 3% hydroxy propylmethacrylate, 40% methyl acrylate and 57% acrylic acid which was 75% sodium acrylate and 25% free acrylic acid. The polymer was made as an aqueous solution of about 35% polymer concentration, and had a molecular weight of around 500,000.

The viscous polymer solution was dry spun through a lubricated, multiple orifice, spinnerette into a temperature of about 250° C. and the fibres were stretched and immediately wound up. They were dry on the surface but contained residual moisture within their structure. Quite quickly after being spun the fibres were cured at 210° C. for 2 minutes. The resultant product was a flexible, high absorbent, fibre.

In alternative processes the amount of methyl acrylate can be reduced to, for instance, 25% and/or methyl or other alkyl methacrylate can be used.

EXAMPLE 10

50gms of a 40% wt/wt solution of a copolymer comprising 43% sodium acrylate, 17% acrylic acid, 37% methyl acrylate and 3% hydroxypropyl methacrylate by weight in water of Brookfield viscosity 60,000cps (at 10rpm) was mixed with 50gms of water and adjusted to a temperature of 40° C. 100gms of a hydrophilic polyether polyisocyanate Hypol RHP 2000 (Grace Rexoline Chemicals Hypol is a trade mark) were rapidly mixed in and the foam expanded over a period of about 2 minutes to a volume of about 400mls. The foam was then baked for 30 minutes to ensure complete reaction. A small piece of this foam was cut off and immersed in cold tap water. It swelled over a period of 2 minutes to about 20 times its original volume. The excess water was squeezed out and the foam dried at 100° C. for 2 hours when it reduced to its original volume. It was again swollen with water to about 20 times its original volume.

We claim:

1. A water absorbent, water insoluble, polymeric element that has a gel capacity of at least 50 grams deionized water per gram dry polymer and that has been made by a process comprising the steps of (a) providing a substantially linear polymer that has been made by polymerization of a water soluble ethylenically unsaturated monomer blend comprising at least 50% by weight monomer that provides carboxylic acid groups and 0.1 to 15% by weight monomer that provides hydroxyl groups that can react with the carboxylic acid groups to form ester cross linkages that contain only carbon and oxygen atoms in the linkages, (b) shaping a solution of the polymer by a shaping step selected from extrusion, coating, impregnation and foaming to shape the linear polymer into the shape of the desired element and then (c) heating the shaped element to cause the said carboxylic and hydroxylic groups to react in the shaped element to form the said cross linkages.

2. An element according to claim 1 in which the monomer that provides the carboxylic acid groups is selected from acrylic acid and water soluble salts thereof.

3. An element according to claim 1 in which the monomer that provides the hydroxylic groups is selected from vinyl alcohol precursor, allyl alcohol, epoxide substituted vinyl monomers and hydroxy alkyl esters of vinyl carboxylic monomers.

4. An element according to claim 1 in which the monomer that provides the hydroxylic groups is selected from hydroxy alkyl esters of (meth) acrylic acid.

5. An element according to claim 1 in which the carboxylic acid monomer is present as a mixture of free carboxylic acid and alkali metal salt groups in the ratio 1:1 to 1:10 and the total amount thereof is at least 40% by weight of the monomers.

6. An element according to claim 1 in which the monomer blend includes 2 to 50% by weight plasticising monomer.

7. An element according to claim 6 in which the plasticising monomer is selected from styrenes, vinyl esters, acrylonitrile and alkyl esters of ethylenically unsaturated acids.

8. An element according to claim 6 in which the plasticising monomer is selected from $C_{1-24}$ alkyl (meth) acrylates in an amount of from 10 to 45% by weight of the monomers.

9. An element according to claim 1 in which the said cross linking reaction is effected by heating the substantially linear polymer at above 150° C.

10. An element according to claim 1 in which the linear polymer is provided as an aqueous solution that has been made by aqueous solution polymerisation.

11. An element according to claim 1 in which the shaping is by extrusion of the solution of the substantially linear polymer and the polymer is substantially immediately precipitated in the shaped element and the shaped element has one dimension at least five times a second dimension.

12. An element according to claim 11 in which the element is a fibre or film.

13. An element according to claim 1 in which the shaping is by impregnating or coating the solution of the substantially linear polymer on to a film or fibrous core to form a polymer product comprising the film or fibrous core coated with the absorbent polymer.

14. An element according to claim 1 in which the shaping is by applying the solution of the substantially linear polymer to a first substrate and laminating a second substrate to the first substrate while the polymer is in solution, and the shaped element comprises a laminate of the first and second substrates bonded by the absorbent polymer.

15. An element according to claim 1 in which the shaping is by incorporating the solution of the substantially linear polymer into a foamable composition and foaming the composition and the shaped element is a foam comprising the swellable polymer substantially uniformly distributed throughout.

16. An element according to claim 1 in which the monomer blend comprises carboxylic acid monomer, 0.1 to 15 % monomer selected from vinyl alcohol, allyl alcohol, epoxide substituted vinyl monomers and hydroxy alkyl esters of vinyl carboxylic monomers, and 2 to 50% plasticizing monomer selected from styrenes, vinyl esters, acrylonitrile and alkyl esters of ethylenically unsatured acids.

17. An element according to claim 16 in which the linear polymer has been made by solution polymerization and the resultant solution shaped either by extrusion as a fiber or film and the polymer has been substantially immediately precipitated or by coating on a film or fibrous core.

18. An element according to claim 16 in which the linear polymer has been made by solution polymerization and the resultant solution was shaped by dry spinning as a fiber to produce a fiber that is substantially dry on the surface but contains at least 10% residual moisture, the fiber is stretched, and the stretched fiber is cured by heating.

19. A water absorbent, water insoluble, polymeric fibre or film that has a gel capacity of at least 50 grams deionized water per gram dry polymer and that has been made by a process comprising (a) providing an aqueous solution of a substantially linear polymer that has been made by polymerization of a water soluble ethylenically unsaturated monomer blend comprising at least 50% by weight (meth) acrylic acid or water soluble salt thereof, 1 to 15% by weight hydroxy acid or water (meth) acrylic acid, and 10 to 45% by weight $C_{1-24}$ alkyl (meth) acrylate, (b) extruding the solution as fibre or film and substantially immediately precipitating the polymer in the extruded fibre or film, and (c) heating the extruded fibre or film to react the carboxylic and hydroxy alkyl groups to form ester cross linkages and thereby render the film or fibre insoluble in water.

20. A fibre or film according to claim 19 in which the fibre or film is dried after the precipitation and before the formation of the cross linkages.

21. A fibre or film according to claim 20 in which the fibre or film is stretched before the formation of the cross linkages.

22. A fibre or film according to claim 20 in which the molecular weight of the linear polymer is 100,000 to 1 million.

* * * * *